United States Patent [19]

Deutch et al.

[11] Patent Number: 5,320,952
[45] Date of Patent: Jun. 14, 1994

[54] ENHANCED GENE EXPRESSION IN RESPONSE TO LACTATION SIGNALS

[75] Inventors: Alan H. Deutch; Victor A. David; Julia B. Wolf, all of Columbia, Md.

[73] Assignee: W. R. Grace & Co.-Conn., New York, N.Y.

[21] Appl. No.: 71,594

[22] Filed: Jun. 2, 1993

Related U.S. Application Data

[63] Continuation of Ser. No. 556,639, Jul. 23, 1990, abandoned, and a continuation-in-part of Ser. No. 410,578, Sep. 21, 1989, abandoned.

[51] Int. Cl.[5] .................. C12N 15/00; C07H 21/00
[52] U.S. Cl. .................. 435/69.1; 435/172.3; 435/320.1; 536/24.1; 935/33; 935/34; 935/36
[58] Field of Search .......... 536/27; 435/69.1, 172.3, 435/320.1; 935/33, 34, 36

[56] References Cited

U.S. PATENT DOCUMENTS

| | | | |
|---|---|---|---|
| 4,666,839 | 5/1987 | Souza | 435/91 |
| 4,675,297 | 6/1987 | Baxter et al. | 435/253 |
| 4,725,549 | 2/1988 | Cooke et al. | 435/243 |
| 5,082,779 | 1/1992 | Rottman et al. | 435/172.3 |

FOREIGN PATENT DOCUMENTS

| | | | |
|---|---|---|---|
| 0201882 | of 0000 | European Pat. Off. | C12N 15/00 |
| WO89/01039 | of 0000 | PCT Int'l Appl. | C12N 15/00 |
| WO88/10304 | of 0000 | PCT Int'l Appl. | |
| WO88/01648 | 3/1988 | PCT Int'l Appl. | C12P 21/00 |

OTHER PUBLICATIONS

Maurer, DNA(1): 1-9 (1985).
Nelson et al., Nature 322: 557-562 (1986).
Camper et al., J. Biol. Chem. 260(22):12246-12251 (1985).
Camper et al., DNA 3(3): 237-249 (1984).
Crenshaw et al., Genes & Dev. 3: 959-972 (1989).
Truong et al., "Isolation and characterization of the human prolactin gene" *The EMBO Journal*, vol. 3 No. 2, pp. 429-437 (1984).
Supowit et al., "Polypeptide hormone regulation of gene transcription: Specific 5' genomic sequences are required for epidermal growth factor and phorbol ester regulation of prolactin gene expression," *Proc. Natl. Acad. Sci.*, vol. 81, pp. 2975-2979 (1984) Biochemistry.
Camper et al., "Hormonal Regulation of the Bovine Prolactin Promoter in Rat Pituitary Tumor Cells," *the Journal of Biological Chemistry* (1985) by The American Society of Biological Chemists, Inc., vol. 260: pp. 12246-12251.
Luck et al., "Synthesis of Bovine Prolactin in *Escherichia Coli,*" *DNA*, vol. 5, No. 1 (1986), pp. 21-28.
Selden et al., "Human Growth Hormone as a Reporter Gene in Regulation Studies Employing Transient Gene Expression," *Mol. Cell. Biol.*, pp. 3173-3182, vol. 6 (1986).
"Ha-ras oncogene expression directed by a milk protein gene promoter: Tissue specificity, hormonal regulation, and tumor induction in transgenic mice"—Andres et al., *Proc. Natl. Acad. Sci.*, vol. 84, pp. 1299-1303 (1987).
Lamming, "Regulating growth of animals," *Nature*, vol. 336, pp. 19-20 (1988).

*Primary Examiner*—Jasemine C. Chambers
*Attorney, Agent, or Firm*—Bharat C. Gandhi

[57] ABSTRACT

An expression method for enhanced recombinant production of a desired protein due to the presence of lactation-signals is provided which comprises cells transformed with a DNA sequence having the desired protein coding sequence under the control of a bovine prolactin promoter and a bovine prolactin distal enhancer sequence. A preferred embodiment uses growth hormone sequences as the desired protein coding sequences. In this embodiment, feed-efficiency of milk-producing animals is improved.

17 Claims, 8 Drawing Sheets

FIG. 1

```
GATCTGGGTCGACCTGCAGGTCAACGGATCTGCAAAAGAGCACATACAAA   -2160
AATTAAGGTAGATAGGCAGTGACATATGAGAAAGACAGATAAGACAGTTA   -2110
TGACATTTTATATAAAATAAGCCTTTTACATTATTTcaacccactccagg   -2060
tctcttgcctggaaaatcccatggatggaggagactggtaggctgcagtc   -2010
catggggtcactaggagtcagacgtgactgagcgacttcactttccttt   -1960
tcagtttcatgcattggagaaggaaatggcaacccactccagtattcttg   -1910
cctggagaaacccagggatgggagagcctggagggctgccgtctatgggg   -1860
tcgcccagagtcagatacgactgaagcgacttAGCAGCAGCAGCAGTTTG   -1810
CATTATTTAGCTATGGCAGTATCCTTTTAACAGGAAATATAGGGCTGTGA   -1760
ATCAGCAAGAAAGCACACAAGAAATTTTACAGAGAAACATGGACCTCTTC   -1710
GGAATCAAATAGATCAGTTGGCCTCCATTGAATAAACAACTTAGGCTTTT   -1660
TAAATTACTTTTTTCCTCGCTATCTACAAAAGGTAAAGCACCTTTAAATT   -1610
TTAAGATTAAGTTGTCAATTCTTAGGGCAGATTTTCCTATTATTAAGTTT   -1560
CAGGAAAGGAGGGGAAATTGGGGCAGCATTAATTTCTTTACAAATGGCAC   -1510
TGTTCTCAACAACTCAGACTTTCACTGTCCAGGGAAAAACAGATACCAAG   -1460
CATGGCATTTTGACCCAGCTTTAAGTTGACGGAGTCTATGTAGCATCATA   -1410
CTTGATTCATTTGATGCAAAATCAGTATTGATTAAGCTAAGGCAGTTAGG   -1360
AGGATAGTTTTTAAGTGGCGTTAGTCTTTGTTATGATTTCTAAGTCCCCA   -1310
TAAGCACACTTGGATAATTGCTAAAGCAAAATACAGCAGGAGAAACTATA   -1260
GAAAATATGAATGCAATAAAAGAGATTATTTTCTTAATGCAGCTCACTT   -1210
GTCAATTTACTCTGAGAGACATATGGTAAAATTGAAACTAAAGGTCACAG   -1160
GCTGCTTGAGATGCATGAACTTAAAAATTAAAGAAAGTCATCAGCAACTT   -1110
GGTCTATATTCATTACCATCATCTCATTCAGGAAATCTCTAAAAGGCAAG   -1060
```

FIG. 1 CONT.

```
TGGAACTTTAGAGCCCATGAAAGATGAATTTTTGTCACCTTGGCCCTAGA   -1010

GTGGCTTGAGGTCAGAGAATTAAAGCTATCATAAGTTAATAACAGTTTGT   -960
             ^g XbaI
GTAACCTTACCCTTAAGGAAAGTGAACATGACTGTCTAGAATTTTGTTTT   -910
       g                                  a
ACTGCATTTACCAGAGTTTGTGTGTGTGTGTATGTGTGTGTGCCCTTG     -860

AAAACCACTGTCACTTCCCCAGTATGAACTCCCTAAAGTTAGGGGTGAGT   -810
       c        ^a       c
TTTGTGTTCATTGTAGAAGAGAGGGCAACGTATGTTGGAGGATTCATTTT   -760
             a
CCAGCCCTCTTCACATCCCTCCTGATTTCTCTTGAAGTGATAAACATTTC   -710

GGTATCTAACTTGACTAATTCTATATCCTTGACATTTAAACTCCCCATCC   -660
                                   a a    a
CACTGTTTCTCAATCTGGGGACGAAAGATATAACTTTACATACATGTTAA   -610
           --    a   c
AATCAAAAGACTTATGTGAAAATGCACATTTTACCACAGAGATATATCCT   -560
        c            -          g
TTTAGAAAGGACAAAACAGAATGTGTAAAAATCAAGAAAAAAAAAATGAG   -510

GAAAATGTATTGAGAGTATAACAGGAACTGAAAATCTTACTTACTCATCC   -460

TTATTCTATATTTCTTAGTATTTAGTGTGTAAATTTTGAAATCTTGACTT   -410

CAGCCAGCAATTTTGAATGAGAATAAAATACTCTTTGATAATACATGAGA   -360

CACCTAAGTGAAAGATAATGCTATATTCAAGAAACTGCAGAGAAATAAAG   -310

GCAAATGTTACAAGAAATGACTGCTATAATTTTATAGTTCCTCTAACTCA   -260
         BglII
AACTAGTCTCCAGATCTCACCATCATTATCTCTCTCATTTCCTTTCAGTC   -210

TAATTAATCAAAATCCTTCCTAGATGTTCATTTCTGGTCAGTATGTCTTC   -160

CTGAATATGAATAAGAAATAGAATACCATTCAATGTTTGAAATTATGGGG   -110

GTAATCTCAATGACGGAAATAGATGACTGGCAAAAGGGAAGGGAATGCCT   -60

GATTAAATATATTCATGAAGATGTCAAAGCCTTATAAAGCCAACATCTGG   -10
         +1
GGAAGAGAAAGCCATAGGACGAGAGCTGGATC
                ***
```

```
                    ↓-1175
BOVINE   AACTAAAGGTCACAGGCTGCTTGAGATGCATGAACTTAAAAATTAAAGAAAGTCATCAGCAACTTGGTCTATATTCATTACCATCATCT
         ||||||||||||||| |||||| |||| ||||  ||||    ||||||||||||||||||||||||||||| |  ||  ||  |||
RAT      AACTAAAGGTCACAAGCTGCTTCAGATGAATGAATCCCCAAATTAAAGAAAGTCATCAGCAACTTCATTATTATTCACCATAATGACAT
                                                   ↑-1730

↓-1085
BOVINE   CATTCAGGAAATCTCTAAAAGGCA--AGTGGAACTTTAGAGCCCATGAAAGA-TGAATTTTTGTCACCTTGGCCCTAGAGTGGCTTGAGGTCA
         |||| ||||||||||||| |||||  ||  ||||||| |||  ||  ||||| |||  |||||||||| |  ||||||||||||| ||||||
RAT      CATTTAGGAAATCTCTAAAA--CATGAGTGGAACTTTGGAGTGCATTAAAAAATGCATTTTTGTCACTATGT-CCTAGAGTGCTTTGGGGTCA
                                                   ↑-1640
```

FIG. 2 pHCprl 2

ENHANCED GENE EXPRESSION IN RESPONSE TO LACTATION SIGNALS

This application is a continuation of application Ser. No. 07/556,639, filed Jul. 23, 1990, now abandoned.

TECHNICAL FIELD

This invention relates to the field of recombinant expression. More specifically it relates to using a promoter and bovine prolactin distal enhancer regulatory sequences to facilitate the expression of desired coding sequences.

When growth hormone, growth hormone-releasing hormone or insulin-like growth factor-I coding sequences are used in the expression system, the invention also relates to the improvement or enhancement of feed-efficiency of milk-producing animals.

BACKGROUND OF THE INVENTION

The polypeptide hormone prolactin is synthesized by specialized cells, lactotrophs, in the anterior pituitary and is a major regulator of lactogenesis. The genes encoding several animal prolactins have been sequenced [human (Cooke et al., J. Biol. Chem., (1981) 256 (8):4007), bovine (Nilson et al., Nucleic Acids Research (1980) 8(7):1561), rat (Cooke et al., J. Biol. Chem., (1980) 255(13):6502)].

Studies using a rat pituitary tumor cell line that constitutively expresses prolactin and growth hormone have suggested that the synthesis of prolactin is regulated transcriptionally by a number of factors including cAMP, epidermal growth factor (EGF), phorbol esters, thyrotropic releasing hormone (TRH), $Ca+2$, dopamine, glucocorticoids and estradiol (Camper et al., J. Biol. Chem. (1985) 260:12246-12251). Elsholtz et al. (Science (1986) 234:1552-1557) and others have used deletion analysis of the rat prolactin promoter region to define two major regulatory regions, both of which respond to a number of these inducing/repressing molecules. Both of these regions have enhancer activity in that they function in either orientation and can activate genes driven by heterologous promoters in rats. The most proximal regulatory region is located within the first 300 bases of the 5' flanking region; the distal enhancer is approximately 1.5 kb from the transcriptional start site (Nelson et al., Nature (1986) 322:557-562).

Previously, 1 kb of 5' flanking sequence has been identified for the bovine prolactin gene. The sequence of the first 250 base pairs of the bovine prolactin 5' flanking region is highly similar to the sequence of the proximal enhancer region of the rat prolactin gene (Camper et al., DNA (1984) 3:237-249). No additional regulatory sequences analogous to the rat distal enhancer region have been reported. In fact, it has been reported that the proximal 250 base pairs contain all the sequence information necessary for regulation by inducing hormones including epidermal growth factor, thyrotropic releasing hormone, and dexamethasone (Camper et al., (supra)).

A number of groups have attempted to use prolactin regulatory sequences to effect expression of heterologous proteins. Nelson et al. (Nature (1986) 322:557) reports the coupling of the rat prolactin promoter to a heterologous gene, and the expression of the hybrid gene in tissue culture.

Palmiter and Brinster, Ann. Rev. Genetics, 20:465-499 (1986) review experiments with gene transfer into the germ-line cells of mice and with gene expression in transgenic mice. Table 4 in this reference refers to expression of a "prolactin/SV40 early region" transgene in pituitary (lactotroph) cells of transgenic mice.

Rottman et al. (PCT88/02463) discloses a method of expressing a non-prolactin gene in a transgenic animal which involves operably linking the gene to a bovine prolactin promoter and introduction into the animal. Since the prolactin promoter is relatively weak, the Rous Sarcoma Virus (RSV) enhancer element was necessary to enhance the transcription rate to an acceptable level. When the RSV enhancer was added, tissue specificity remained intact, but regulation by EGF and dexamethasone was blunted. The use of a viral enhancer is not nearly as desirable as the use of a native enhancer. However, the native bovine prolactin enhancer element was not known prior to this invention.

BRIEF DESCRIPTION OF THE INVENTION

This invention provides new 5' flanking sequences of the bovine prolactin gene. Specifically, it provides distal enhancer regulatory sequences.

This invention also relates to expression of a desired coding sequence in cells and transgenic animals and the methods to do so. To effect expression, a transcriptional unit is formed by operably linking (i) a promoter sequence, (ii) a bovine prolactin distal enhancer sequence and (iii) a desired coding sequence and introducing the transcriptional unit into cells. The use of this expression system facilitates the enhancement of expression, in response to lactation signals, of a myriad of coding sequences. While any promoter sequence is capable of effecting expression in this system, a bovine prolactin promoter sequence is preferred.

It is the object of this invention to replace the viral enhancer previously used in conjunction with the bovine prolactin promoter with the native prolactin distal enhancer. Lactation signals such as EGF induce bovine prolactin promoter activity. When viral enhancers are used, uninduced expression is enhanced, but the effect of lactation signals are blunted. The use of a native bovine prolactin distal enhancer not only enhances uninduced expression, but also further enhances the effect of lactation signals.

This invention provides a native bovine prolactin distal enhancer which enhances the action of the bovine prolactin promoter. This enhancement is at least 3-5 times greater than expression directed by the promoter alone and is inducible by lactation signals.

It is a further object of this invention to provide a transgenic animal whose induced expression of a desired coding sequence is controlled by physiological state rather than external factors. Since this expression system is induced whenever lactation signals (e.g., EGF, cAMP) are provided, in a transgenic animal these signals are provided naturally during lactation, therefore the animal's physiological state can control expression. However exogenous administration of inducing molecules is also contemplated by this invention.

In one embodiment, growth hormone, growth hormone-releasing hormone and insulin-like growth factor-I coding sequences are used in the expression system. This provides an aspect of the invention which relates to the improvement or enhancement of feed-efficiency of milk-producing animals.

BRIEF DESCRIPTION OF THE DRAWINGS

FIG. 1 (2 pages) shows the DNA sequence of the 2.2 kb bovine prolactin 5' flanking region, which includes the promoter and distal enhancer.

FIG. 2 shows the DNA sequence homology between bovine and rat prolactin distal enhancer regions.

DETAILED DESCRIPTION OF THE INVENTION

Figure 3:
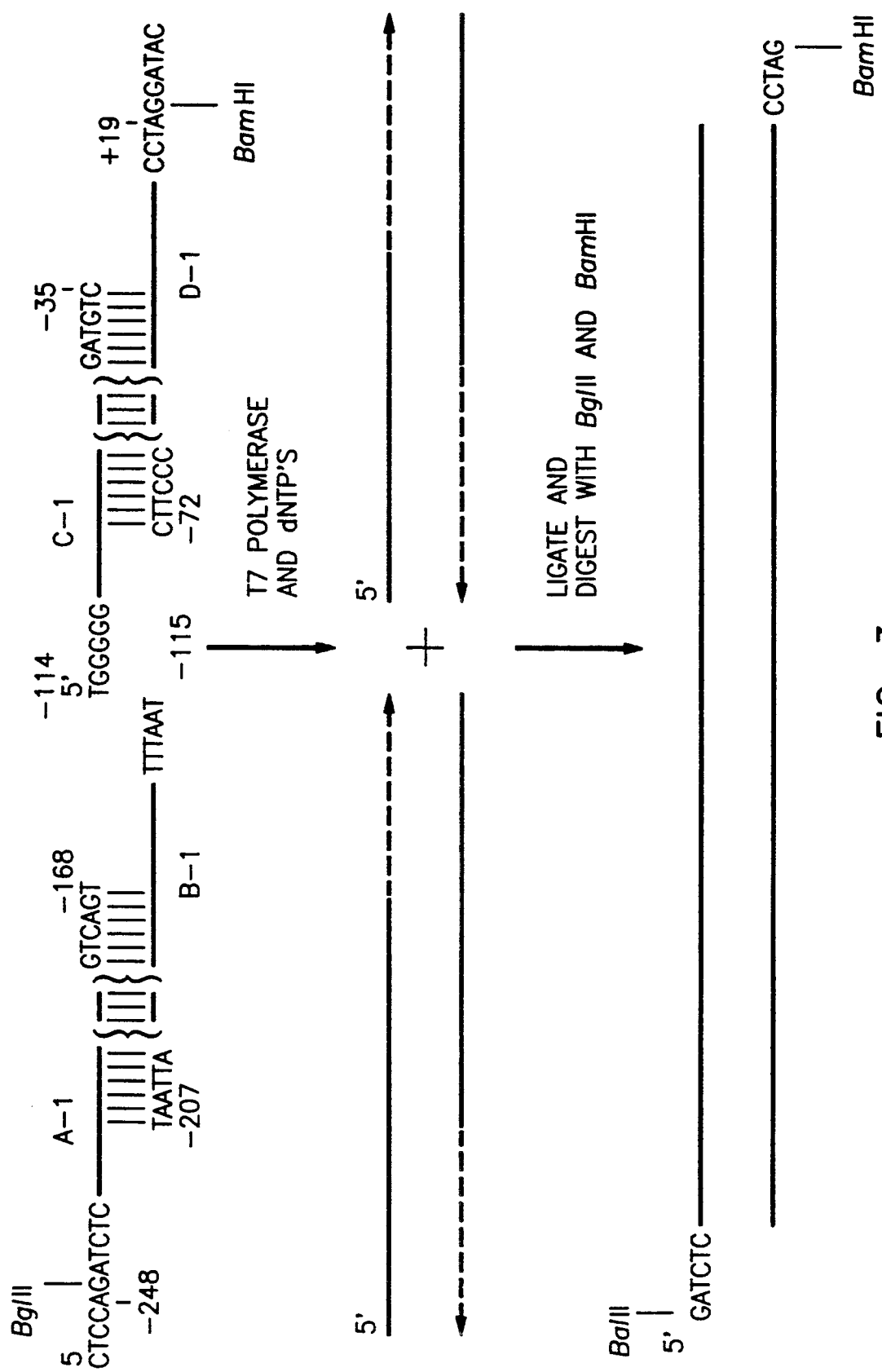
FIG. 3 illustrates the preparation of the bovine prolactin promoter from four synthetic oligonucleotides.

As indicated above, this invention provides approximately 1 kb of new sequence 5' of the bovine prolactin gene, which includes sequences encompassing distal enhancer regulatory sequences. The expression methods of the present invention allow enhanced expression of a desired coding sequence in response to lactation signals. The method comprises forming a transcriptional unit by operably linking (i) a promoter sequence; (ii) a bovine prolactin distal enhancer sequence; and (iii) a desired coding sequence; and introducing the transcriptional unit into cells.

A. Definitions

As used herein, "lactation signals" refer to signals that occur during or prior to lactation, such as EGF, dexamethasone, TRH. Therefore, the expression system of the invention is inducible rather than constitutive, which is advantageous in both cell culture and transgenic systems. In cell culture, cell growth can proceed until an appropriate cell mass is obtained before the inducing agent is added and expression is enhanced. In transgenic animals, this allows for the enhanced expression of gene products only at appropriate times in the animals' development. Lactation signals can be native or exogenous.

"Desired Coding Sequence" refers to any coding sequence. This can include sequences for any peptide or protein such as hormones, growth factors, structural proteins, enzymes, receptors, oncogenes. Preferred coding sequences include growth hormone, growth hormone-releasing factor, insulin-like growth factor-I, parathyroid hormone (PTH) and PTH-like peptide (PTH-LP). A most preferred coding sequence is bovine growth hormone.

"Transcriptional Unit" refers to a segment of DNA that includes 5' regulatory sequences, including enhancer and promoter regions, and a structural gene, which is capable of initiation and termination of transcription by RNA polymerase. Introns, 3' regulatory and internal regulatory sequences may also be included.

"Operably linking" refers to a juxtaposition such that the ordinary functions of the operably linked materials may be carried out. Thus an enhancer and promoter operably linked to a coding sequence refers to a configuration wherein the coding sequence can be expressed under control of the promoter, and the enhancer effects a comparable or higher level of expression than that allowed with promoter alone in compatible hosts. Additionally, the enhancer confers a comparable or higher level of tissue specificity to the expression of the coding sequence.

"Promoter Sequence" refers to a region on a DNA molecule to which an RNA polymerase binds and initiates transcription. Many promoter sequences are known and include metallothionein promoter, and bovine growth hormone promoter. The preferred promoter sequence is the bovine prolactin promoter sequence.

"Bovine Prolactin Promoter Sequence" refers to a sequence containing proximal control sequences derived from the bovine prolactin gene or their functional equivalents. The proximal control sequences of this gene are substantially similar to nucleotides $-248$ to $-1$ of FIG. 1.

"Bovine Prolactin Distal Enhancer Sequence" refers to distal control sequences derived from the bovine prolactin genes or their functional equivalents. The presence of a bovine prolactin distal enhancer was unknown prior to this invention. The bovine prolactin distal enhancer is 79% homologous to the rat prolactin distal enhancer as shown in FIG. 2. The bovine prolactin distal enhancer is located approximately 1 kb upstream from the transcription start site, while the homologous rat distal enhancer sequence is located approximately 1.5 kb from the start of transcription. Based on homology to the rat sequence, the distal enhancer sequences of the bovine prolactin gene are substantially similar to nucleotides $-1175$ to $-996$ of FIG. 1. Deletion mapping has identified the bovine prolactin distal enhancer to comprise a sequence substantially similar to nucleotides $-1124$ to $-985$ of FIG. 1. The boundaries of the enhancer sequence can be flexible as long as the sequence has the ability to enhance expression levels above that of constructs without enhancer.

"Cells" refers to cells which have been or are intended to be recipients of new DNA sequences, most commonly in the form of plasmids, but including other transferable DNA forms as well. In this regard, these terms refer not only to the immediate recipient, but also its progeny. Progeny includes product cells of cell division, as well as of other reproductive mechanisms. Progeny includes cells which contain substantially identical DNA sequence content, as well as those wherein the DNA has been altered by accidental or deliberate mutation. It is understood that such mutations may occur as a matter of course in the production of progeny. All progeny which maintain the functionality of the initial transformant, most commonly the ability to produce a specific desired protein, are included in this definition. Cells include all eucaryotic cells. Eucaryotic cells can include transgenic animals as well as cell cultures. Preferred cells are those of transgenic bovine, ovine, porcine, equine and caprine. The most preferred cell is that of a transgenic bovine.

"Introduction of the transcriptional unit into cells" refers to any means useful in recombinant DNA technology for transforming cells. This includes but is not limited to transfection, electroporation, blasting, microinjection.

The following abbreviations have been used throughout in describing the invention.

| | |
|---|---|
| bGH | bovine growth hormone |
| bp | base pairs |
| °C. | degrees centigrade |
| $Ca^{+2}$ | calcium ion |
| cAMP | cyclic AMP |

| | -continued |
|---|---|
| cDNA | complementary deoxyribonucleic acid |
| dATP | deoxyadenosine triphosphate |
| dCTP | deoxycytosine triphosphate |
| dGTP | deoxyguanosine triphosphate |
| DNA | deoxyribonucleic acid |
| DTT | dithiothreitol |
| dTTP | deoxythymidine triphosphate |
| EGF | epidermal growth factor |
| hGH | human growth hormone |
| IGF-I | insulin-like growth factor-I |
| kb | kilobase pair |
| $MgCl_2$ | magnesium chloride |
| ml | milliliter |
| mM | millimolar |
| μg | microgram |
| μl | microliter |
| NaCl | sodium chloride |
| PCR | polymerase chain reaction |
| pmole | picomole |
| PTH | parathyroid hormone |
| PTH-LP | parathyroid hormone-like peptide |
| RSV | *Rous Sarcoma* Virus |
| TRH | thyrotropic releasing hormone |
| U | units |
| % | percent |

B. General Description

The present invention offers a substantial improvement in recombinant protein production by virtue of enhancing the effect of promoters, particularly the bovine prolactin promoter with the native bovine prolactin distal enhancer. Prior to this invention, the bovine prolactin distal enhancer was unknown. The use of all bovine sequences in transgenic bovines is especially desirable.

Previously, use of the bovine prolactin promoter had to be enhanced by viral enhancers. Use of viral enhancers blunted the effects of inducing molecules such as EGF on the promoter. The cloning and characterization of the bovine prolactin distal enhancer has allowed for the first time the enhancement of the bovine prolactin promoter by an enhancer element which does not blunt the effect of inducing molecules. The effect of enhancer/promoter expression is at least 3-5 times greater than promoter expression alone. Furthermore, the use of extended 5' flanking regions is desirable for achieving the position-independent, high-level expression of gene products in transgenic animals (Grosveld, et al., *Cell* (1987) 51(6):975).

The bovine prolactin promoter and bovine prolactin distal enhancer are placed in the same vector (usually a commonly known plasmid, such as pUC12). The distance between the promoter and enhancer can vary greatly. The most preferable distance between promoter and enhancer for this invention is between 0 and 1 kb. The enhancer can be in either orientation on the vector.

A useful expression vector is one which contains restriction sites downstream of the promoter to permit insertion of a desired coding sequence. Such a vector contains replication sites operable in bacteria, to permit amplification of the host vector and coding sequence insert fragments. The coding sequences ligated into the restriction sites may be either cDNA sequences or genomic fragments containing introns if the vector is to be introduced into eucaryotic cells capable of processing introns.

The expression vectors, according to the invention, are introduced into cells. Preferred cells include eucaryotic cells. Eucaryotic cells also include transgenic animals, such as bovine, ovine, porcine, equine, or caprine. Introduction of the vector into cells can be via a number of different transformation techniques known in the art, such as calcium phosphate precipitate transfection, DEAE-dextran transfection, blasting, infection, electroporation, microinjection. In general, replication in the cells relies on integration of the appropriate sequences into the host genome, but self-replicating vectors may also be used. Transient expression in cells is also possible. The transformed cells can be selected in some manner to determine whether the desired coding sequence has been introduced.

Another aspect of the invention is the use of the expression system for the expression of growth hormone, growth hormone-releasing hormone, or insulin-like growth factor-I in transgenic cows. The ability to enhance production of any of these proteins specifically in response to lactation signals results in increased efficiency of milk production (i.e., more milk produced per feed utilized) Peel et al., *J. Nutr.* (1981) 111:1662. By using the expression system of the invention, regulation of production of the proteins will in part be controlled by the physiological state of the animal as opposed to unnatural or external factors, such as dietary zinc or implants. Moreover, exposure of the animal to elevated levels of growth hormone will be limited to the time corresponding to lactation. However, exogeneous administration of lactation signals is also contemplated by this invention.

EXAMPLES

Many of the techniques used to practice the invention, such as restriction digests, ligation conditions, transformation and transfection protocols and different vectors to use, are widely known and practiced in the art, and most practioners are familiar with the standard resource materials which describe conditions and procedures. The examples are written in observation of such knowledge and incorporate by reference procedures considered conventional in the art.

The following examples are intended to illustrate the invention, without acting as a limitation on its scope.

Example 1

Preparation of a Synthetic Bovine Prolactin Promoter

A. The prolactin promoter (based on the sequence described by Camper et al. (supra)) was constructed from four oligonucleotides synthesized on an Applied Biosystems 380B DNA Synthesizer using B-cyanoethyl phosphoramidite chemistry and purified by polyacrylamide gel electrophoresis using standard procedures. The four oligonucleotides recreate the proximal 248 bases of the bovine prolactin 5' flanking region as shown in FIG. 1. The sequences of the four oligonucleotides are as follows:

oligonucleotide A-1:
5' CTC CAG ATC TCA CCA TCA TTA TCT CTC TCA TTT CCT TTC AGT CTA ATT AAT CAA AAT CCT TCC TAG ATG TTC ATT TCT GGT CAG T 3' oligonucleotide B-1:
5' TAA TTT CAA ACA TTG AAT GGT ATT CTA TTT CTT ATT CAT ATT CAG -continued

GAA GAC ATA CTG ACC AGA AAT GAA CAT CTA GGA AGG ATT TTG ATT
AAT 3' oligonucleotide C-1:

5' TGG GGG TAA TCT CAA TGA CGG AAA TAG ATG ACT GGC AAA AGG GAA
GGG AAT GCC TGA TTA AAT ATA TTC ATG AAG ATG TC 3' oligonucleotide D-1:

5' CAT AGG ATC CAG CTC TCG TCC TAT GGC TTT CTC TTC CCC AGA TGT
TGG CTT TAT AAG GCT TTG ACA TCT TCA TGA ATA TAT TTA ATC AGG
CAT TCC CTT C 3'

The oligonucleotides were designed such that the 5' end of the synthetic double-stranded fragment represents the natural BglII site at position −248; and the 3' end is an artificial BamHI site created by the insertion of three bases, GGA, between the T at position +18 and the T at position +19 as shown in FIG. 1. The two sets of oligonucleotides A-1/B-1 and C-1/D-1 were separately annealed, extended with T7 DNA polymerase (Sequenase TM, US Biochemical) to generate blunt ends, and then ligated together as illustrated in FIG. 3. The ligation reaction was digested with BamHI and BglII to generate ends suitable for cloning, and the desired fragment was gel purified using standard procedures. The synthetic DNA fragment was subcloned into the BamHI site of pUC13 resulting in plasmid p102.

To confirm that the DNA sequence was correct, the fragment was then subcloned as an EcoRI/HindIII fragment into M13mp18 and M13mp19 and the DNA sequence was determined by the dideoxynucleotide-chain-termination method of Sanger et al. (*Proc. Natl. Acad. Sci.* (1977) 74:5463–5467) using fluorescently-labelled primers (Applied Biosystems, Inc.). Template DNA was prepared as described by Ausabel et al. (*Current Protocols in Molecular Biology*, (1987) New York: John Wiley & Sons). For the A and C reactions, 0.2 pmole of template DNA was annealed with 0.4 pmole primer in 10 mM Tris-Cl, pH 7.5, 10 mM MgCl2, and 50 mM NaCl in a total volume of 5 µl. For the G and C reactions, volumes and amounts of these and all subsequent steps were scaled up threefold. The annealing reactions were incubated at 55° C. for 5 minutes and allowed to cool to room temperature. Working deoxy- and dideoxynucleotide mixes were prepared as follows: each mix contained 1 mM dATP, 1 mM dCTP, 1.5 mM 7-deazadGTP (Boehringer Mannheim), 1 mM dTTP, and 50 µM of one the four dideoxynucleotides. For the A and C reactions, 1.5 µl of the appropriate nucleotide mix and 1.0 µl of Sequenase TM dilution (1.0 µl Sequenase enzyme, 10–12 U/ml, 4.5 µl 0.1 M DTT, 3.5 µl 5X Sequencing Buffer: 50 mM Tris-Cl pH 7.5, 50 mM MgCl2, and 250 mM NaCl) were added and incubated at 37° C. for 5 minutes. The four extension reactions were then pooled and ethanol precipitated, washed with 70% ethanol and dried briefly. The DNA pellets were resuspended in 5.0 µl of water, 1.0 µl of 50 mM EDTA, and 5.0 µl deionized formamide. Prior to loading, the reactions were heated at 95° C. for 8 minutes (with the caps off to reduce the volume). The reactions were then run on an 8.3% urea, 6% polyacrylamide gel (19:1, acrylamide:bis) and analyzed on an Applied Biosystems, Inc. 370A DNA Sequencer. Overlapping DNA sequences were identified with the Seqman TM program of DNASTAR TM (DNASTAR Inc.).

Example 2

Cloning of Bovine Prolactin Distal Enhancer

To obtain additional 5' flanking sequences, a bovine genomic DNA library in λEMBL3 was prepared from sperm DNA from the registered Holstein bull, Valiant (American Breeders Services) using standard protocols (Stratagene Inc.). The library was screened for prolactin sequences using either a [$^{32}$P] end-labelled oligonucleotide, bPRL 1-10 that represents the nucleotide sequence encoding the first nine amino-terminal amino acids of the mature prolactin protein or a random-primer labelled synthetic promoter fragment.

The sequence of bPRL 1-10 is as follows:

5' TTG CCA GGC CCA TTG GGA CAG ACG
GG GT

Figure 5:
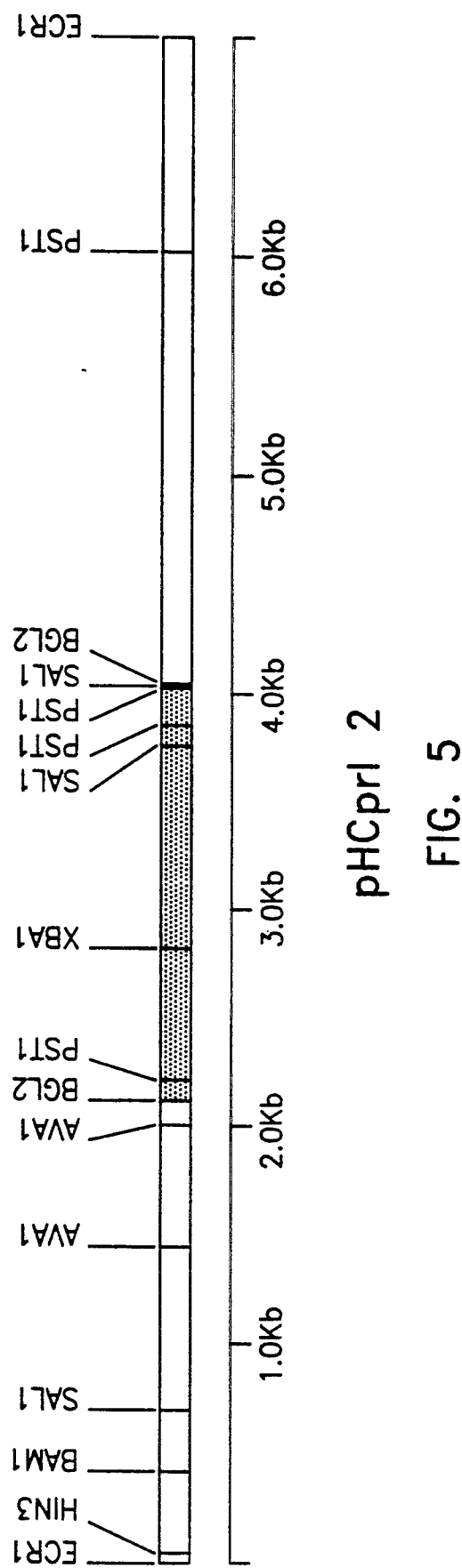
FIG. 5 illustrates the linearized restriction enzyme map of plasmid pHCpr12.

One recombinant plaque that hybridized to both probes was identified. The bacteriophage DNA from this plaque was amplified and analyzed by restriction enzyme digestion. This clone, λprlL8, in addition to containing the entire structural gene, contained 2.0 kb of 5' flanking prolactin sequences on a BglII DNA fragment. The BglII DNA fragment was initially subcloned as part of a larger HindIII fragment into pBR322, yielding pL8H2. The 2 kb BglII DNA fragment was then subcloned from pL8H2 into a BglII digested pBR322 derivative, pHC79. The restriction enzyme map of the resultant plasmid, pHCpr12, is shown in FIG. 5. The shaded area in FIG. 5 represents the 2.0 kb BglII fragment. pHCpr12 was deposited with the American Type Culture Collection, 12301 Parklawn Drive, Rockville, Md. on Aug. 23, 1989 and received accession number 68082.

Figure 4:
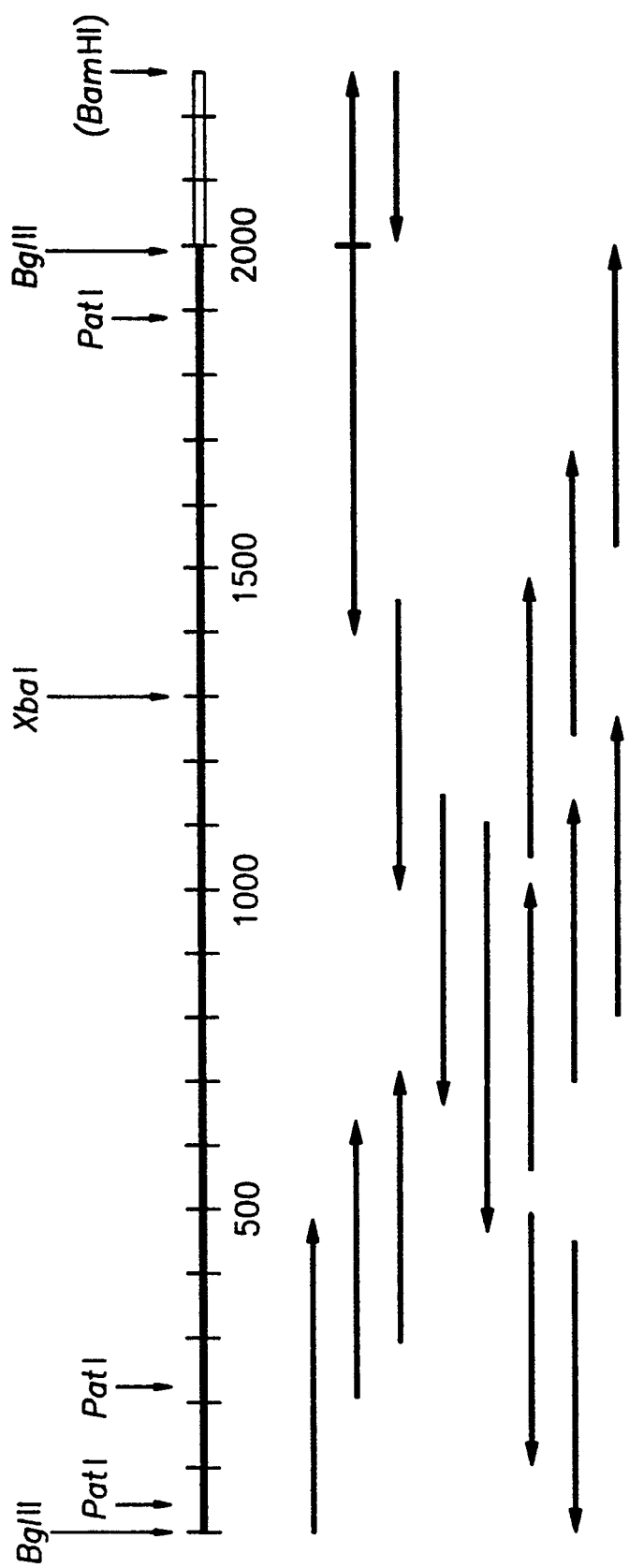
FIG. 4 shows the sequencing strategy of the 2.2 kb bovine prolactin 5' flanking sequence.

The 2.0 kb 5' flanking prolactin DNA fragment was also subcloned into an M13 vector and sequenced using Exonuclease III (Promega) generated deletions using the procedure described by Henikoff (*Gene* (1984) 28:351-359). The sequencing strategy is illustrated in FIG. 4. The sequencing protocol is the same as used in Example 1 above. Both strands of the 2.0 kb BglII fragment were sequenced using Exonuclease III-generated overlapping deletion fragments. The arrows show the direction of extension and the extent of sequence data generated. The open box represents the synthetic promoter fragment which was separately cloned and sequenced in both directions. The sequence of the 2.0 kb BglII fragment as well as the synthetic promoter region is shown in FIG. 1. Single base pair differences between our sequence and that reported by Sakai et al. (*Genes Dev.* (1988) 2:1144-1154) are shown with the base pair differences in lower case under the affected base. A caret (Λ) denotes the insertion of a base and a dash (—) a missing base. The sequence 5' of base −984 had never before been identified. The sequence was searched for sequence homologies to the rat enhancer sequence using the DNA alignment program of Wilbur & Lipman (*Proc. Natl. Acad. Sci.* (1983) 80:726-730). The results of the homology search revealed an approximately 150 base-pair region of similarity between the bovine sequence (−1175 to −996) and the rat enhancer sequence (−1730 to −1559) as shown in FIG. 2. The homology between the two sequences is 79% over that region. This high degree of homology strongly suggested that the region from −1175 to −996 of the bovine sequence is a distal enhancer.

Example 3

Construction of Prolactin:hGH Expression Vectors

Figure 6:
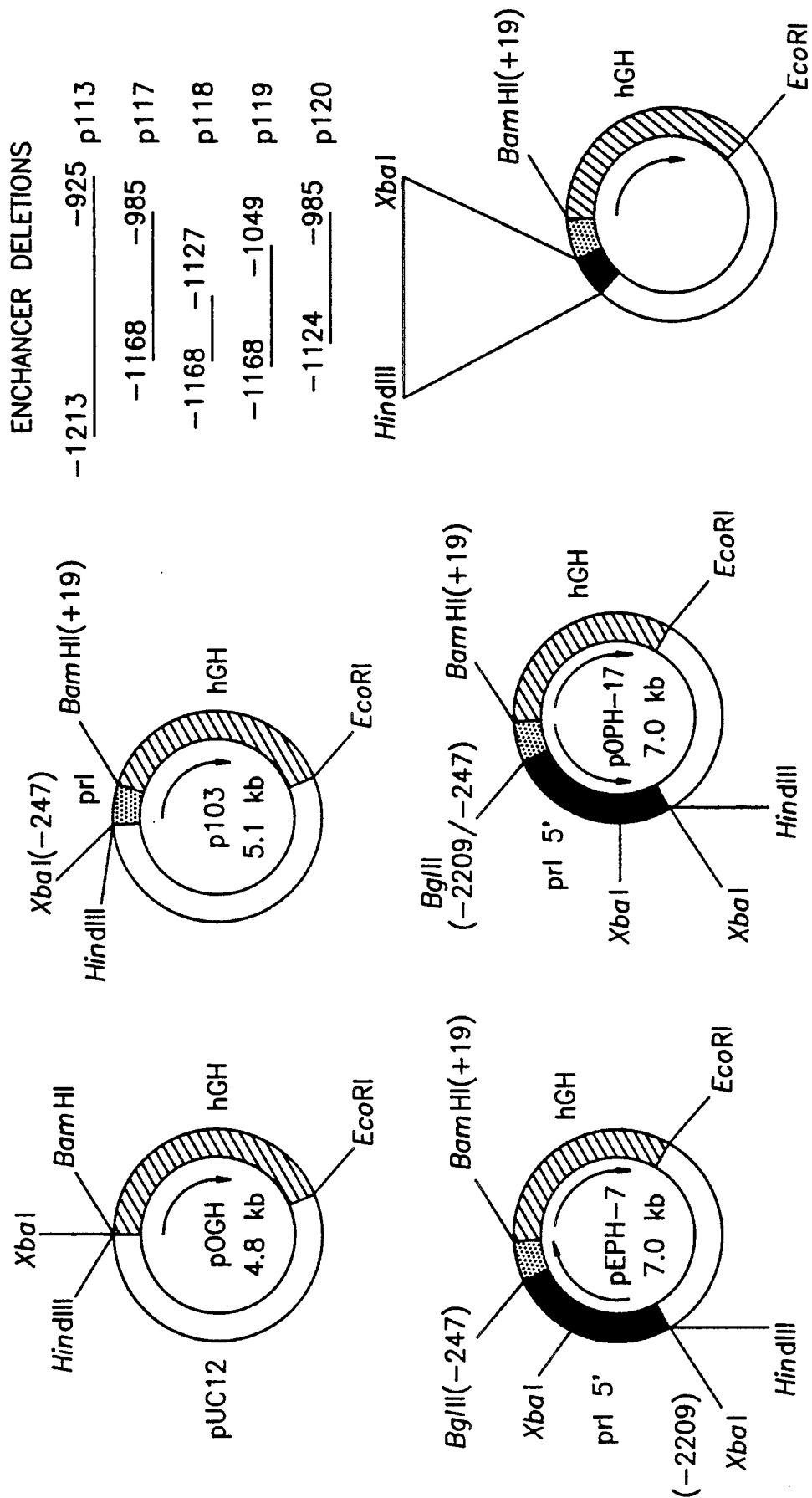
FIG. 6 illustrates the prolactin:hGH expression constructs.

Human growth hormone (hGH) was used as a model coding sequence to evaluate the expression system.

pOGH pOGH was the control plasmid. It is the promoterless hGH structural gene (Nichols Institute Diagnostics, CA) as shown in FIG. 6.

p103 p103 contains the bovine prolactin promoter and the hGH gene as shown in FIG. 6. The HindIII/BamHI fragment from p102 described in Example 1 containing the synthetic bovine prolactin promoter was ligated into Hind III/BamHI digested pOGH to yield p103.

pEPH-7 pEPH-7 contains the bovine prolactin promoter, the 2 kb bovine prolactin 5′ flanking sequence which includes the distal enhancer oriented in the same direction as the promoter and the hGH gene as shown in FIG. 6. The construction of pEPH-7 included a three-way ligation of 1) the BglII fragment from pL8H2 containing the 2.0 kb of 5′ flanking sequence (described in Example 2), 2) the BamHI/Sau3A fragment from p103 containing the bovine prolactin promoter and 3) BamHI-digested pOGH. The appropriate combination, order and orientation of ligated fragments were identified by restriction digestion.

pOPH-17 pOPH-17 is analogous to pEPH-7 except that the 2.0 kb fragment containing the distal enhancer is in the opposite orientation as shown in FIG. 6. pOPH-17 was prepared in the same ligation mixture as pEPH-7 and was selected by its specific restriction pattern.

p113 p113 contains nucleotides −1213 to −925 (300 bp) of the bovine prolactin 5′ flanking sequence which includes the distal enhancer, along with the bovine prolactin promoter and hGH gene as shown in FIG. 6. A 5′ deletion of the 2.0 kb BqlII fragment in M13mp18 was generated, wherein the sequences from −2 kb to −1213 were deleted. The naturally occurring XbaI site at −925 was utilized to excise the 300 bp as a HindIII (donated from the M13 multiple-cloning site)/XbaI fragment. This HindIII/XbaI fragment was cloned into HindIII/XbaI-digested p103 to place the distal enhancer directly upstream from the promoter region.

p117 p117 contains nucleotides −1168 to −985 (183 bp) of the bovine prolactin 5′ flanking sequence which includes the distal enhancer, along with the bovine prolactin promoter and hGH gene as shown in FIG. 6. The enhancer fragment was generated using polmerase chain reaction (PCR) amplification (Saiki et al., *Science* (1988) 239:487-491). The oligonucleotide primers used were:

PRL-1178:
5′TTGAAACTAAAGCTTACAGGCTG3′

PRL-982C:
5′TATCTAGAATTCTCTGACCTCAAGCC3′.

Plasmid pEPH-7 was used as a template to generate the PCR fragments. The PCR amplification product was digested with HindIII and XbaI and cloned into plasmid p103 to generate plasmid p117.

p118 p118 contains nucleotides −1168 to −1127 (41 bp) of the bovine prolactin 5′ flanking sequence, along with the bovine prolactin promoter and hGH gene as shown in FIG. 6. The 5′ flanking sequence fragment was generated as described for p117 using PCR amplification. The oligonucleotide primers used were PRL-1178 (used for p117) and

PRL-1099C:
5′CCAAGTTGCTGATGACTTT-CTAGAAT3′.

p119 p119 contains nucleotides −1168 to −1049 (119 bp) of the bovine prolactin 5′ flanking sequence, along with the bovine prolactin promoter and hGH gene as shown in FIG. 6. The 5′ flanking sequence fragment was generated as described for p117 using PCR amplification. The oligonucleotide primers used were PRL-1178 (used for p117) and

PRL-1041C:
5′CATGGGCTCTAGAGTTCCACTTGC3′.

p120 p120 contains nucleotides −1124 to −985 (139 bp) of the bovine prolactin 5′ flanking sequence which includes the distal enhancer, along with the bovine prolactin promoter and hGH gene as shown in FIG. 6. The enhancer sequence was generated as described for p117 using PCR amplification. The oligonucleotide primers used were:

PRL-1128:
5′AGAAAGCTTTCAGCAACTTGGTC3′ and PRL-982C (used for p117).

Example 4

Transfections of Prolactin-hGH Constructs Cell culture conditions

GH3 rat pituitary cells (obtained from American Type Culture Collection) were maintained in the absence of $CO_2$ in complete WRC 935 ® medium (Amicon Division of W. R. Grace & Co.-Conn.), 5-10% fetal calf serum (Gibco, #230-6140), and 100 unit/ml Penicillin-Streptomycin (Gibco, #600-5140). Additional supplements as indicated in the text were 10 nM epidermal growth factor (Collaborative Research).

DNA transfections

GH3 cells were transfected with cesium chloride-purified plasmid DNA by a modification of the method described by Camper et al. (supra). Approximately $1-3 \times 10^6$ cells per well were plated in 6-well tissue culture plates or 60 mm cell culture dishes (Falcon) and grown for 24 hours prior to transfection. The cells were washed three times with WRC 935 medium without supplements, and the DNA solution was added in a dropwise fashion to the center of the plate. The DNA solution contained the appropriate amount of DNA diluted into a total volume of 200 μl: 100 μl of WRC 935 medium/50mM Tris pH 7.5 (without supplements) and 100 μl of 200 μg/ml DEAE-Dextran (Pharmacia #17-0595-01) diluted in saline. After 30 minutes at 37° C., the DNA solution was removed, the cells were washed once with WRC 935 medium (without supplements) and 5 ml of complete WRC 935 medium was added with or without inducer. The tissue culture plates were wrapped in plastic wrap and incubated at 37° C. for up to 6 days. Aliquots of supernatant (200–300 μl) were removed at various times after transfection and assayed for hGH activity.

Time course experiments were performed with prolactin:hGH constructs alone in triplicate. Analyses of the prolactin enhancer deletion constructs involved cotransfection with pRSVcat plasmid DNA (ATCC) to correct for transfection efficiencies. Crude extracts were prepared in 0.25 M Tris-HCl pH=8.0 and chloramphenicol acetyltansferase (CAT) enzyme activity was determined using the liquid scintillation counting (LSC) assay with N-butyryl coenzyme A (Promega) as the cofactor (Seed et al., Gene (1988) 67:271–277). Units of hGH activity were calculated as ([hGH]ng/ml/(CAT units × 100).

Optimum cell numbers and DNA concentrations were determined using plasmid p103 and pXGH-5, a control plasmid containing the mouse metallothionein promoter fused to the hGH structural gene (Nichols Institute Diagnostics). Gene expression was proportional to the amount of DNA added up to 0.5 μg. Additional DNA inhibited transfection efficiency.

Example 5

Human Growth Hormone Assays

The model coding sequence in the previous examples is human growth hormone (hGH). Unlike chloramphenicol acetyltransferase, a bacterial gene with an unstable mRNA in eukaryotic cells, the hGH mRNA is very stable. In addition, the protein product is secreted into the medium which not only simplifies assay procedures, i.e., cell extracts are not needed, but also allows rapid sampling of multiple time points for individual transfections.

An hGH radioimmunoassay was performed using a monoclonal antibody-based assay essentially as described (Nichols Institute Diagnostics, #40-2205). No cross reactivity to bovine growth hormone in the fetal calf serum or to endogenous rat growth hormone produced by the pituitary cells could be detected. Samples were typically diluted at least 1:2 in 100% fetal bovine serum. Accumulation of hGH in the supernatants could be detected up to at least 200 hours after transfection. The following table indicates the results of a typical hGH assay:

TABLE 1

EFFECT OF PROLACTIN ENHANCER ON THE EXPRESSION OF HGH IN TISSUE CULTURE CELLS
[hGH]ng/ml/CAT units × 100

|      | −EFG | +EGF |
|------|------|------|
| POGH | 0    | 0    |
| P103 | 0.66 | 8.6  |
| pEPH-7 | 3.0 | 20.6 |
| p113 | 1.9  | 18.9 |
| p117 | 1.2  | 20.2 |
| p118 | 0.48 | 16.5 |

TABLE 1-continued

EFFECT OF PROLACTIN ENHANCER ON THE EXPRESSION OF HGH IN TISSUE CULTURE CELLS
[hGH]ng/ml/CAT units × 100

|      | −EFG | +EGF |
|------|------|------|
| p119 | 0.23 | 11.0 |
| p120 | 1.9  | 23.0 |

The data indicate that plasmid p120 contains a 139 bp (nucleotides −1124 to −985) region having full enhancer activity capable of enhancing lactation specific expression. Constructs containing this 139 bp sequence and additional contiguous sequences also showed full enhancer activity (i.e., p117, p113, and pEPH7). These constructs demonstrated both enhanced levels of basal expression and EGF-induced expression. Constructs p118 and p119 do not contain the entire sequence from nucleotides −1124 to −985, and they do not have the effect of enhancing basal level expression. Constructs p118 and p119 have lower levels of promoter activity in the uninduced state than construct p103 with the promoter fragment alone. Without wishing to be bound by any theory, these data suggest that a repressor sequence is at least partially contained on nucleotides −1168 to −1049. In the induced state, however, the level of hGH activity is higher than in the absence suggesting that the sequences do respond to EGF.

Example 6

Cloning of Bovine Growth Hormone

The bovine genomic library described in Example 2 was used to obtain bovine growth hormone coding sequences. The library was screened using a [$^{32}$P] end-labelled oligonucleotide probe for the 5′ flanking region of the bovine growth hormone gene. The DNA sequence of the oligonucleotide probe corresponds to a highly conserved region observed in the bovine, human and rat growth hormone genes, about 140 bp upstream from the cap site. This region may represent a thyroid hormone binding site or the glucocorticoid responsive site. Thus, this probe might be expected to detect not only the bovine growth hormone gene but also other genes that are similarly regulated. λbGH11 was a bacteriophage which harbored the bovine growth hormone coding sequences. A BamHI fragment containing the bGH gene was isolated from λbGH11 and ligated into BamHI digested pBR322 to yield pBBGH1.

Example 7

Figure 7:
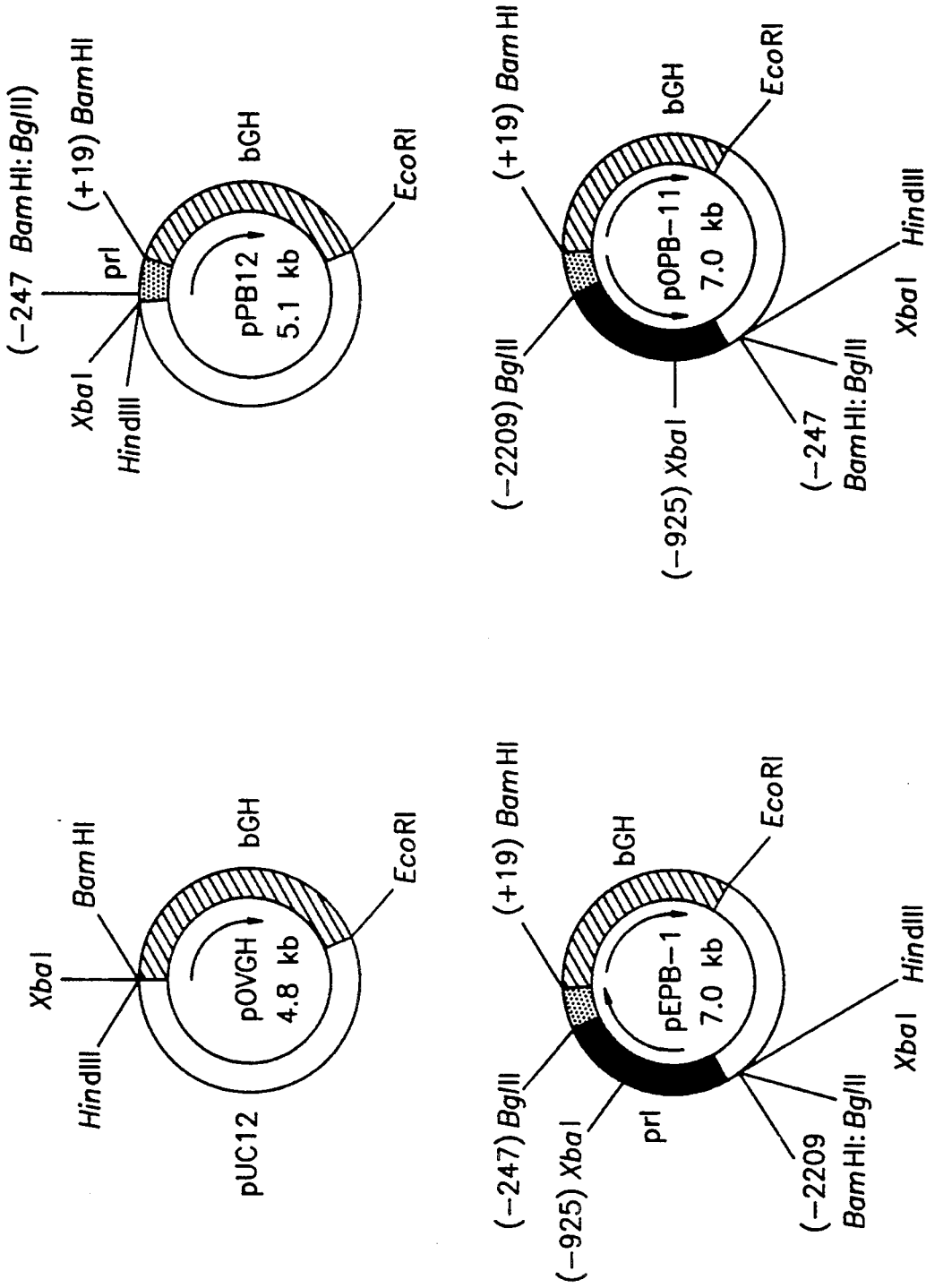
FIG. 7 illustrates the prolactin:bGH expression constructs.

Construction and Expression of Prolactin:bGH Expression Vectors pPB12 pPB12 contains the bovine prolactin promoter and the bGH gene as shown in FIG. 7. pPB12 was constructed by digesting p103 (from Example 3) with BamHI and EcoRI and ligating in a BamHI/EcoRI fragment containing bGH which was isolated from pBBGH1.

pOVGH pOVGH was the control plasmid. It is the promoterless bGH structural gene as shown in FIG. 7. pOVGH was constructed by replacing the BamHI/EcoRI fragment of pOGH containing hGH with a BamHI/EcoRI fragment from pPB12 containing bGH.

pEPB-1 pEPB-1 contains the bovine prolactin promoter, the 2 kb bovine prolactin 5' flanking sequence which includes the distal enhancer oriented in the same direction as the promoter and the bGH gene as shown in FIG. 7. This plasmid was constructed by digesting pEPH7 with BamHI and EcoRI to remove the hGH gene. A BamHI/EcoRI fragment containing the bGH gene was isolated from pPB12 and ligated into BamHI/EcoRI digested pEPH7.

pOPB-11 pOPB is analogous to pEPB-1 except that the 2.0 kb fragment containing the distal enhancer is in the opposite orientation as shown in FIG. 7. This plasmid was derived from pOPH-17 by replacing the hGH gene with the bGH gene from pPB12 as described above for pEPB-1. The transfections of the prolactin:bGH constructs were performed as described for the prolactin:hGH constructs in Example 4.

Competitive radioimmune bGH assays were performed using the polyclonal antibody-based assay essentially as described (*Cambridge Medical Technology*, #IV725). The following table indicates the results of a typical bGH assay. The high background of bGH in the absence of DNA is due to the bGH present in the fetal calf serum used to make WRC 935 complete medium.

TABLE 2

Effect of Prolactin Enhancer on the Expression of bGH in Tissue Culture Cells
[bGH] (ng/ml)

|  | 72 hrs. | 96 hrs. | 120 hrs. |
| --- | --- | --- | --- |
| No DNA |  |  |  |
| −EGF | 4.2 | 6.8 | 5.6 |
| +EGF | 4.2 | 4.4 | 4.8 |
| pOVGH-2 |  |  |  |
| −EGF | 5.8 | 6.0 | 6.8 |
| +EGF | 5.9 | 5.8 | 7.8 |
| pPB12 |  |  |  |
| −EGF | 7.4 | 8.6 | 10.8 |
| +EGF | 18.0 | 21 | 19 |
| pEPB-1 |  |  |  |
| −EGF | 11.2 | 12 | 18.4 |
| +EGF | 14.8 | 22 | 36 |
| pOPB-11 |  |  |  |
| −EGF | 10.3 | 16 | 31 |
| +EGF | 27 | 33 | 58 |

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A purified and isolated bovine prolactin distal enhancer element comprising nucleotides −1124 to −985 of the DNA sequence as depicted in FIG. 1.

2. The purified and isolated bovine prolactin distal enhancer element of claim 1 additionally comprising contiguous DNA sequences to nucleotides −1124 to −985 selected from nucleotides −2209 to −1125 and −984 to +19 as depicted in FIG. 1.

3. A method of expressing a desired coding sequence comprising:

(a) forming a transcriptional unit by operably linking:
 (i) a promoter sequence;
 (ii) a bovine prolactin distal enhancer element comprising nucleotides −1124 to −985 of the DNA sequence as depicted in FIG. 1; and
 (iii) a desired coding sequence; and
(b) introducing said unit into cells.

4. The method of claim 3, wherein said distal enhancer element additionally comprising contiguous DNA sequences to nucleotides −1124 to −985 selected from nucleotides −2204 to −1125 and −984 to +19 as depicted in FIG. 1.

5. The method of claim 3, wherein the cells are eucaryotic.

6. The method of claim 3, wherein said desired coding sequence is growth hormone.

7. The method of claim 6, wherein said growth hormone is bovine growth hormone.

8. The method of claim 3, wherein basal level of expression is greater than expression of a transcriptional unit without the bovine prolactin distal enhancer sequence.

9. The method of claim 3, wherein the amount of expression is increased in the presence of regulatory factors.

10. The method of claim 9, wherein the regulatory factor is epidermal growth factor or thyrotropic releasing hormone.

11. A method for regulating gene expression comprising (a) forming a transcriptional unit by operably linking:
 (i) a promoter sequence;
 (ii) a bovine prolactin distal enhancer element comprising nucleotides −1124 to −985 of the DNA sequence as depicted in FIG. 1; and
 (iii) a desired coding sequence;
(b) introducing the transcriptional unit into cells; and
(c) enhancing expression of the polypeptide of the desired coding sequence in response to a bovine lactation signal.

12. The method of claim 11 wherein the cells are eucaryotic.

13. The method of claim 11 wherein said bovine lactation signal is selected from the group of native or exogenous signals.

14. A method of claim 13 wherein said bovine lactation signal is selected from the group of EGF, dexamethasone and TRH.

15. A method of claim 11 wherein said promoter sequence is the bovine prolactin promoter sequence.

16. A method for regulating bovine gene expression of claim 11 additionally comprising contiguous DNA sequences to nucleotides −1124 to −985 selected from nucleotides −2209 to −1125 and −984 to +19 as depicted in FIG. 1.

17. A method of expressing a desired coding sequence comprising:

(a) forming a transcriptional unit by operably linking:
 (i) a bovine prolactin promoter sequence;
 (ii) a bovine prolactin distal enhancer element comprising nucleotides −1124 to −985 of the DNA sequence as depicted in FIG. 1; and
 (iii) a desired coding sequence; and
(b) introducing said unit into cells.

* * * * *